US012724041B2

(12) United States Patent
Chamanzar et al.

(10) Patent No.: US 12,724,041 B2
(45) Date of Patent: Sep. 1, 2026

(54) HIGH-DENSITY IMPLANTABLE NEURAL PROBES

(71) Applicant: CARNEGIE MELLON UNIVERSITY, Pittsburgh, PA (US)

(72) Inventors: Maysamreza Chamanzar, Pittsburgh, PA (US); Zabir Ahmed, Pittsburgh, PA (US); Jay Reddy, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 822 days.

(21) Appl. No.: 17/291,017

(22) PCT Filed: Nov. 5, 2019

(86) PCT No.: PCT/US2019/059835
§ 371 (c)(1),
(2) Date: May 4, 2021

(87) PCT Pub. No.: WO2020/097056
PCT Pub. Date: May 14, 2020

(65) Prior Publication Data

US 2022/0043028 A1 Feb. 10, 2022

Related U.S. Application Data

(60) Provisional application No. 62/766,828, filed on Nov. 5, 2018.

(51) Int. Cl.
*G01R 1/073* (2006.01)
*A61B 5/25* (2021.01)
(Continued)

(52) U.S. Cl.
CPC ............ *G01R 1/07314* (2013.01); *A61B 5/25* (2021.01); *A61B 5/293* (2021.01); *H01J 37/3174* (2013.01); *A61B 2562/125* (2013.01)

(58) Field of Classification Search
CPC . G01R 1/07314; A61B 5/25; A61B 2562/125; A61B 5/24; A61B 5/291;
(Continued)

(56) References Cited

U.S. PATENT DOCUMENTS 6,834,200 B2 * 12/2004 Moxon ................ A61N 1/0551 607/116
7,941,202 B2 * 5/2011 Hetke .................. A61N 1/0476 607/116
(Continued)

FOREIGN PATENT DOCUMENTS

WO 2011090842 A2 7/2011

OTHER PUBLICATIONS

International Search Report and Written Opinion for International Patent Application No. PCT/US2019/059835 mailed on Apr. 21, 2020, 8 pages.

*Primary Examiner* — Adam Z Minchella
*Assistant Examiner* — Ashleigh Lauren Kern
(74) *Attorney, Agent, or Firm* — KDW FIRM PLLC

(57) ABSTRACT

Disclosed here are two approaches for implementing neural probes that consist of a thin, high-density Parylene C-based probe on a stainless steel shuttle. In a first approach, the high density Parylene C probe is microfabricated separately and is then affixed to a planar or curved stainless steel shuttle. In a second approach, the high-density probe is monolithically fabricated on a stainless steel shuttle by micromachining the stainless steel substrate.

4 Claims, 11 Drawing Sheets

(51) Int. Cl.
*A61B 5/293* (2021.01)
*H01J 37/317* (2006.01)

(58) Field of Classification Search
CPC .......... A61B 2503/40; A61B 2562/046; A61B 5/686; A61B 5/6868; H01J 37/3174; A61N 1/0536
See application file for complete search history.

(56) References Cited

U.S. PATENT DOCUMENTS 8,927,876 B2* 1/2015 Johnson ............... A61N 1/0541 607/57
2007/0123765 A1* 5/2007 Hetke .................. A61N 1/0476 600/378
2010/0331935 A1* 12/2010 Tabada ..................... A61N 1/05 600/377
2013/0090542 A1* 4/2013 Kipke .................... A61B 5/685 607/116
2013/0303873 A1* 11/2013 Voros ................... A61N 1/0551 604/20
2014/0257052 A1* 9/2014 Muller ................. A61B 5/6868 600/378
2014/0288458 A1* 9/2014 Yoon ...................... A61B 5/388 607/116
2014/0378993 A1* 12/2014 Shah ........................ A61N 1/05 428/172
2015/0133761 A1* 5/2015 Vetter .................. A61B 5/6868 607/139
2015/0148644 A1* 5/2015 Vaidyanathan ....... A61M 37/00 607/116
2016/0074655 A1 3/2016 Mercanzini et al.
2016/0211381 A1* 7/2016 Kurokawa ............. H10D 89/10
2017/0128015 A1* 5/2017 Rogers ................. A61B 5/6868
2017/0172438 A1* 6/2017 Lieber ...................... A61N 1/05
2017/0209898 A1* 7/2017 Henneken ............. B06B 1/0292

* cited by examiner (C)

(B)

(A)

HIGH-DENSITY IMPLANTABLE NEURAL PROBES

RELATED APPLICATIONS

This application is a national phase filing under 35 U.S.C. § 371 claiming the benefit of and priority to International Patent Application No. PCT/US2019/059835, filed on Nov. 5, 2019, which claims benefit of US provisional patent application No. 62/766,828, filed Nov. 5, 2018. The entire contents of these applications are incorporated herein by reference.

BACKGROUND OF THE INVENTION

Due to the remarkable similarity in dimensions and structure of the non-human-primate (NHP) brain to its human counterpart, high density neural recordings from NHP brains can potentially lead to understanding of neural basis of brain function and dysfunction, in humans. There is a growing need for high density, mass producible, implantable neural probes for high temporal and spatial resolution recording in primates. While recent efforts have been focused on devising high density probes for neural recordings in rodents, there has been very limited progress in development of neural probes for the large primate brain.

Most existing rigid probes for rodents are based on microfabrication on silicon, leveraging very well developed and long established nano and microfabrication processes used to implement electronic and MEMS/NEMS devices. However, primate brains are larger in size and, as a result, deep brain penetration in NHPs requires longer probes than in rodents, while maintaining resilience to buckling during implantation. Therefore, the design principles, material platforms, and fabrication processes for the rodent probes cannot be directly translated for deep-brain neural interlaces intended for NHPs brains. While silicon based neural probes have been reported for primate brain, those probes have short implantable length (~3 cm) and, as such, are unable to record from deeper regions of NHP brain. Apart from silicon, probes fabricated on polymer platform have also been reported for primate brain recording. However, such probes require manual assembly into specific cylindrical shapes before they can be implanted into the brain.

Long aspect ratio, high-density and robust neural probes are in high demand for deep cortical recording in primates. Such probes are required to have high rigidity and mechanical resilience to penetrate deep into the brain. Silicon, due to its brittleness, is not suitable as a substrate material for such long probes due to the risk of shattering inside the brain during and after implantation.

SUMMARY OF THE INVENTION

As a material platform for the shank of NHP neural probe, stainless steel is biocompatible and offers significantly better mechanical properties compared to silicon, namely, higher modulus of rupture, flexural strength and endurance limit. As a result, unlike silicon, a shank made of stainless steel is more robust and less vulnerable to breakage and therefore, more reliable for manipulation and implantation. For these reasons, stainless steel has been widely used in prosthetic and biomedical devices. However, micromachining of stainless steel has not been developed as much as silicon microfabrication. The best commercially available stainless steel probes for use in NHPs (i.e. the U-Probe and the V-Probe from Plexon Inc.) are hand assembled, which limits the channel density and makes them very expensive.

Disclosed herein are novel neural probes for implantation in NHP brains manufactured by integrating high channel density microfabricated polymer-based probes with stainless steel substrates. Bioresorbable polymers are used to bind a Parylene C probe to a stainless steel shuttle, which provides rigidity during insertion and subsequently releases the flexible probe from the substrate once it is implanted into the brain.

Also disclosed herein is a novel microfabrication and micromachining process to realize stainless steel-based probes monolithically microfabricated on stainless steel substrates, as shown in FIG. 1. This high throughput process will facilitate realization of neural probes with microscopic features on stainless steel, enabling high resolution recording from deep cortical regions in non-human primates.

DETAILED DESCRIPTION OF THE INVENTION

Figure 1:
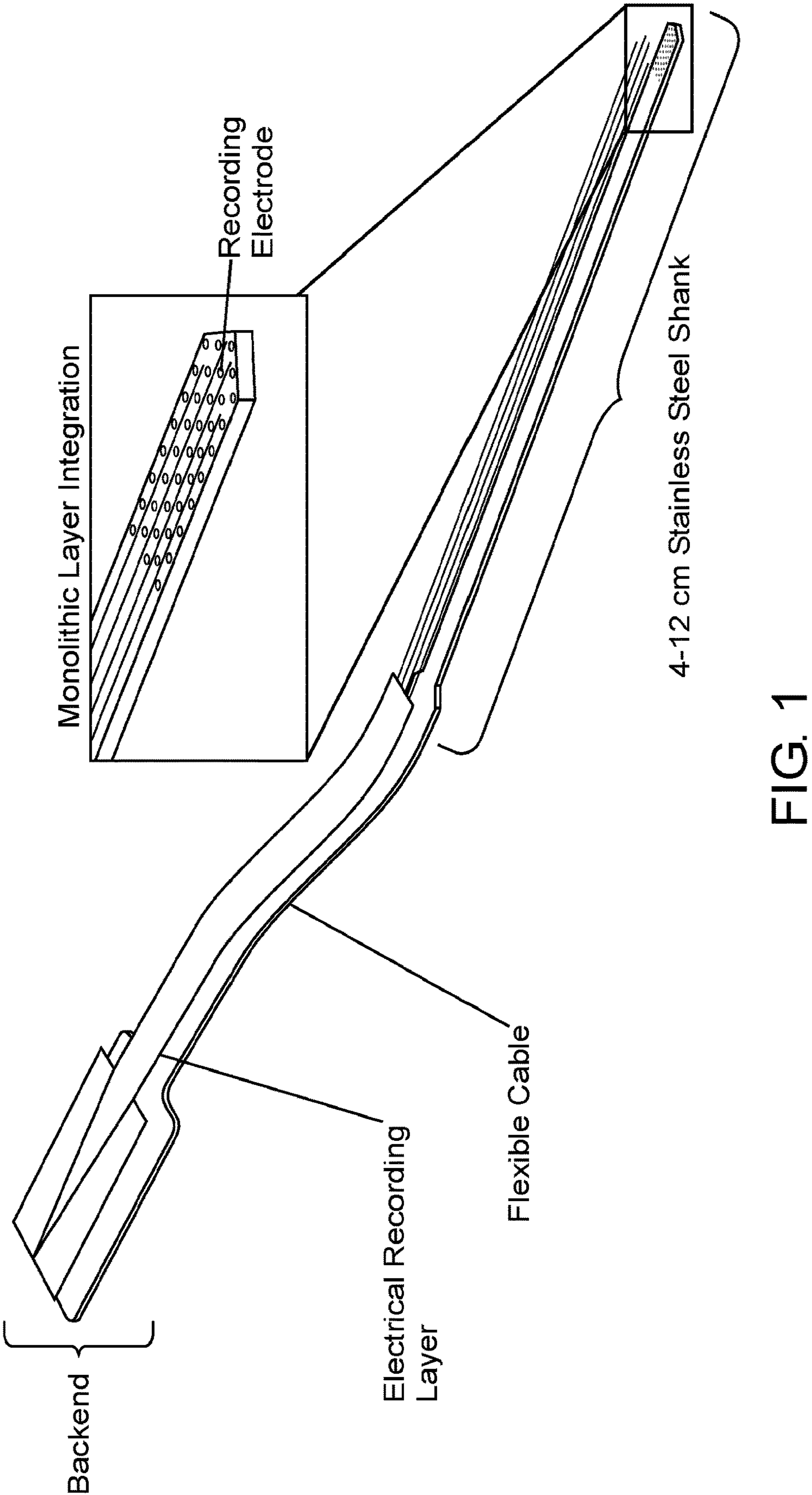
FIG. 1 shows an overall view of a neural probe in accordance with the invention.
Figure 2:
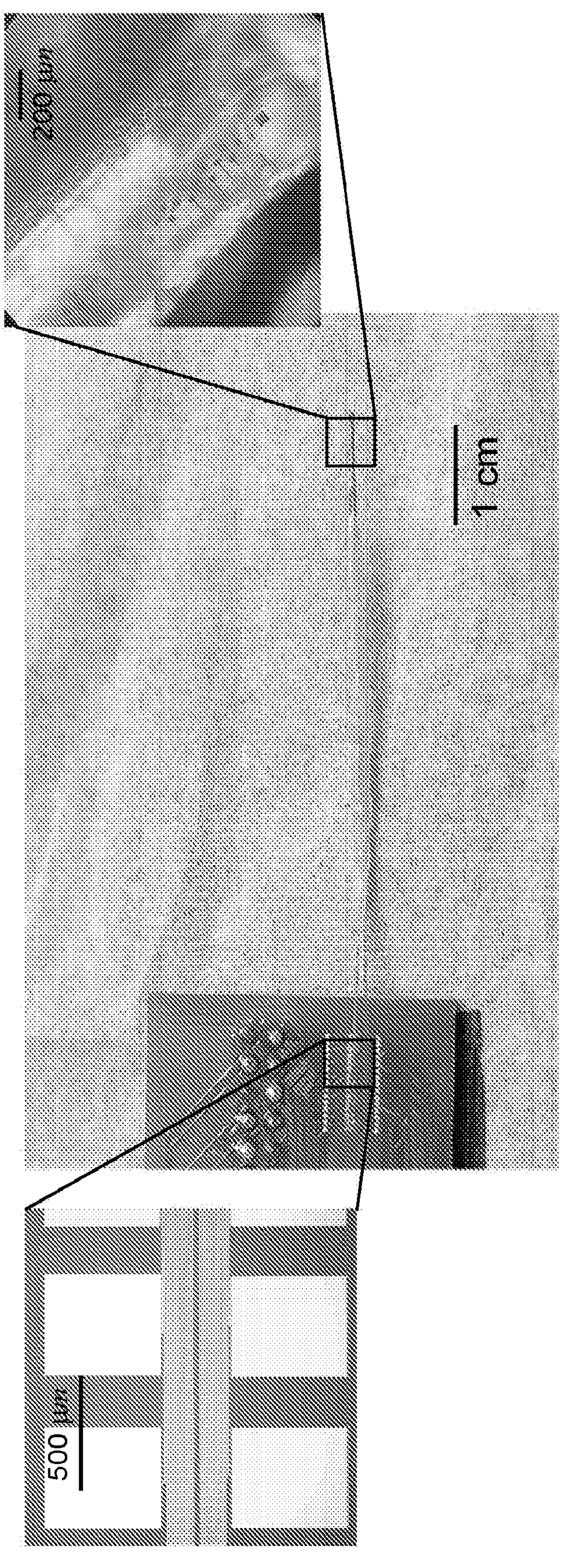
FIG. 2 is an example of probe in accordance with the invention showing the tip of the probe in magnified inset.

Disclosed herein is a novel neural probe design for non-human-primates based on two embodiments, one embodiment comprising post-fabrication integration of high-density neural probes with stainless steel substrates and a second embodiment comprising monolithic integration of high density Parylene-based probes with stainless steel material platform.

In preferred embodiments, the neural probes of this invention take advantage of two different material platforms, namely, a polymer, preferably Parylene C, and stainless steel. The probes are preferably primarily fabricated on Parylene C, a polymer commonly used in biomedical devices due to its flexibility, mechanical strength, and biocompatibility. While the flexibility of neural probes composed of Parylene are suitable for chronic recording, the low rigidity of such probes poses difficulties in implantation due to buckling. Different bioresorbable coatings have been proposed to provisionally increase the rigidity of such flexible polymer-based probes to aid with insertion in rodent brains. However, the mechanical strength required for safe implantation in NHP brains is not achievable only by using bioresorbable coatings on flexible probes.

A first embodiment comprises post-fabrication assembly of high density flexible polymer probes on stainless steel shuttles using a bioresorbable adhesive. The stainless steel shuttle provides the rigidity for insertion and it can then be retrieved after implantation because the bioresorbable adhesive is dissolved once the probe is implanted. This enables the potential for long-term high-density recording using these probes in primate brains, thus minimizing tissue damage and glial scarring. In this embodiment, the neural probes and methods of manufacture integrate a flexible polymer-based probe on a stainless steel shuttle. Polyethylene Glycol (PEG) is preferably used as a bioresorbable adhesive to hold the polymer-based probe on the shuttle during implantation. The stainless steel shuttle can be retracted post-implantation after the PEG dissolves inside the brain, releasing the flexible probe. Using this technique, the polymer-based probe can be mounted on a 3D stainless steel shuttle, for example, on a cylindrical shuttle such that the probe can record from different directions. The flexible probe can potentially record long-term neuronal activity without causing significant tissue damage in a NHP brain.

A second embodiment comprises a novel microfabrication process to realize high aspect ratio, high-density neural probes monolithically integrated on stainless steel substrates. This method requires direct deposition and processing of a Parylene probe stack on a stainless steel wafer followed by deep etching of stainless steel to singulate each of the hybrid probes from the wafer. This highly scalable microfabrication process deposits microscopic features directly on a stainless steel substrate, thereby resolving the yield-limiting issues plaguing the commercial stainless steel probes. In addition to electrical neural probes, the disclosed technology can serve as a new paradigm for implementing next generation multi-modal neural interfaces and prosthetic devices using stainless steel.

It should be noted that all dimensions used in the following descriptions are exemplary in nature and are not meant to be limits on the scope of the invention. Further, the invention is described using Parylene C as the preferred polymer, but it should be realized that other polymers may be used as well.

The probes in accordance with this invention, in some embodiments, consist of 4-12 cm long stainless steel shanks with a width of approximately 260 microns. The probes can have any number of microelectrodes defined thereon, but in practice, an upper limit of up to 128 microelectrodes is practical. The microelectrodes may be distributed in any one of several arrangements within a 1-2 mm active region near the tip of the probe. The electrodes may also be distributed along the entire implanted length of the shank to enable simultaneous recording from different cortical layers or brain regions simultaneously. An example of such a probe is shown in FIG. 1.

High-resolution lithography techniques are used to microfabricate probes consisting of electrodes with, in some embodiments, 11.2 micron diameter and 50 micron inter-electrode spacing. At the backend of the device, two rows of high-density bondpad arrays with 600 micron pitch defined on a printed circuit board are provided to interface with the recording electronic circuitry outside of the brain. In some embodiments, the polymer probe may have a thickness of 10 microns which makes it highly flexible and also ensures minimal reaction in brain tissue after implantation. A stainless steel cannula with a 500 micron outer diameter and a 300 micron inner diameter serves as the implantation shuttle for the Parylene probe. The probe, with high density channels fabricated on a hybrid polymer-stainless steel platform can potentially record long term neuronal activity from deep seated regions of a NHP brain with single-unit resolution.

In a first embodiment of the invention the Parylene probe and the stainless steel shuttle are fabricated separately and joined together. In this embodiment, an optimized high-yield process to fabricate high channel count Parylene probes on a silicon substrate is explained in reference to FIG. 3. In View (A) of FIG. 3, a thin layer of Parylene C 302 is deposited on a substrate wafer 300, preferably silicon, to a thickness of 5 microns using a chemical vapor deposition process. Alternatively, Polyimide, PMMA or PDMS may be used. In View (B) of FIG. 3, a metal stack 304 consisting of 5 nm of Platinum, 120 nm of Gold and 5 nm of Platinum is then deposited and lithographically patterned to define the interconnects and electrodes on the Parylene C film 302. The Pt—Au—Pt stack is preferred as the Platinum layers adhere well to the Parylene, while the Gold layer acts as the conductor. However, different conductors and adhesion materials could be considered for cost reasons or if using a different insulation polymer. Thereafter, as shown in View (C) of FIG. 3, another thin film 306 of insulating Parylene is deposited to a thickness of 5 microns.

Figure 3:
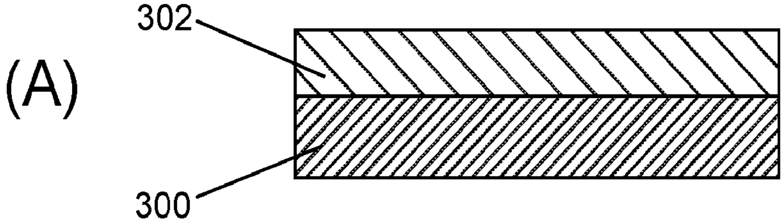
FIG. 3 shows a step-by-step fabrication process for probes in accordance with a first embodiment of the invention in which the probes are fabricated on a silicon substrate and thereafter transferred to a stainless steel shuttle.
Figure 3:
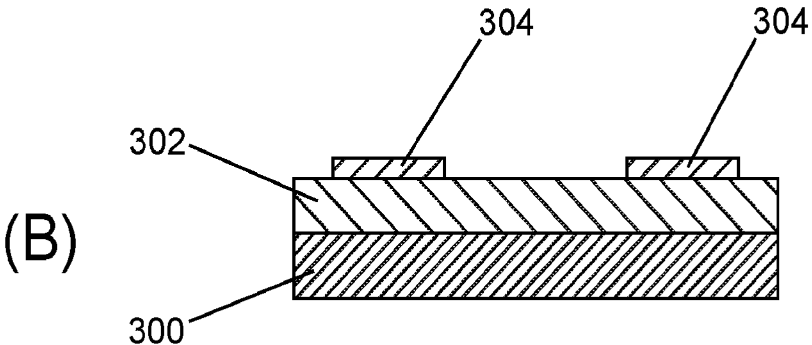
Figure 3:
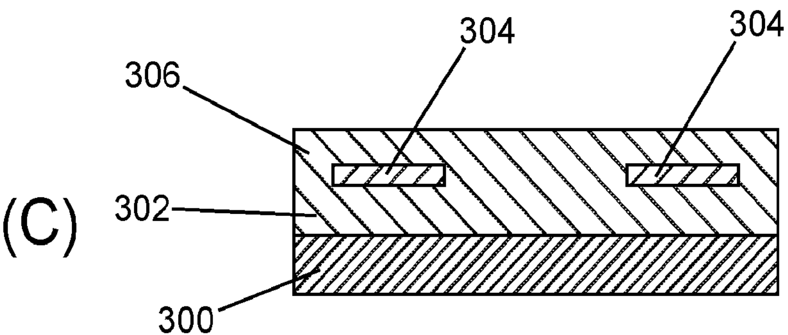
Figure 3:
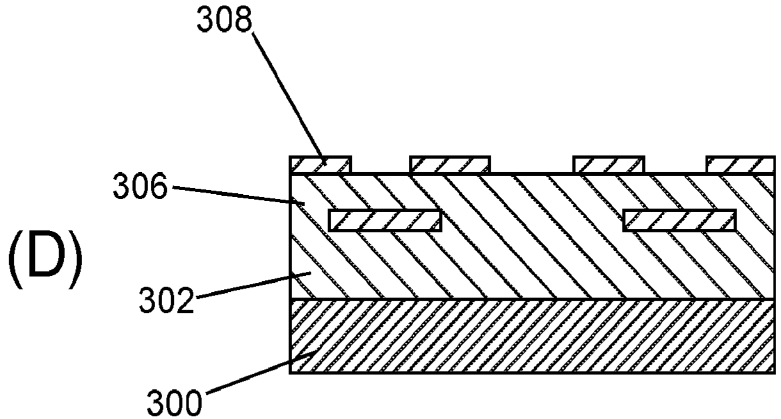
Figure 3:
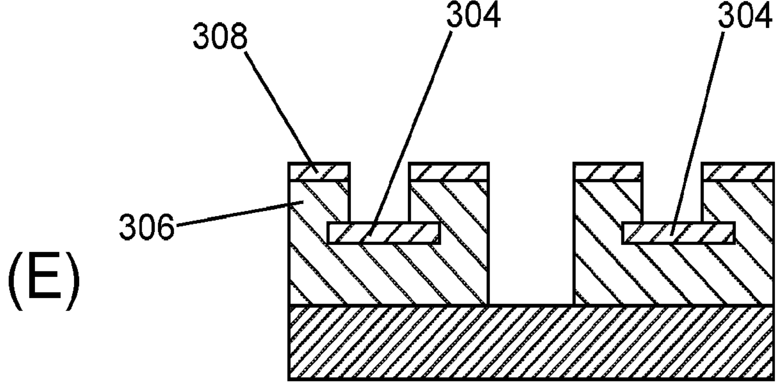
Figure 3:
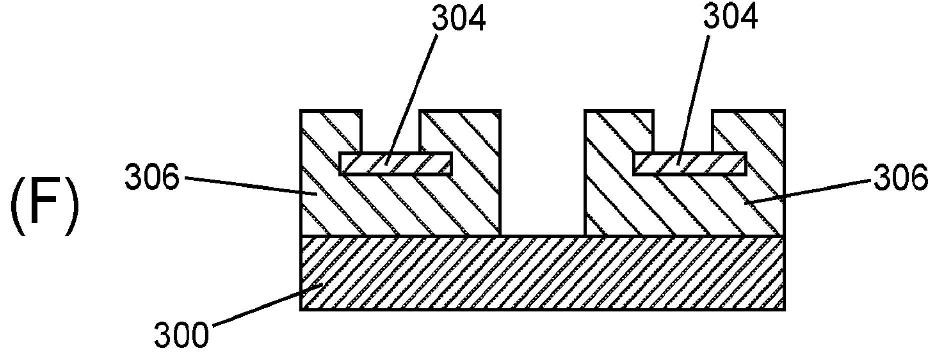
Figure 3:
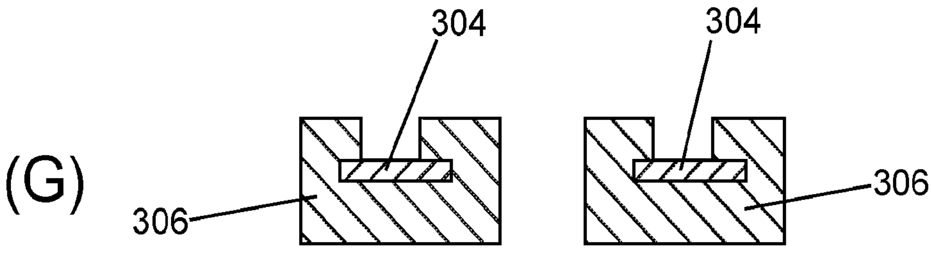

In View (D) of FIG. 3, a hardmask of Chromium 308 is deposited on the insulating layer of Parylene 306 for subsequent Parylene etching. The Chromium hardmask 308 is photolithographically patterned to define the probe outline as well as electrode recording sites and bondpad openings. Chromium is necessary to provide selectivity to oxygen plasma. The surface is etched with plasma to define the outlines of the probes. The surface is temporarily covered in Chromium to protect the probes while we "etch" the outlines. Alternatively, Aluminum may be used. The common mask in conventional microfabrication is photoresist. Here, the dilemma is that Parylene C is also a polymer similar to photoresists, which are also polymers. Therefore, both the mask and the Parylene layer would get etched if oxygen plasma were used, resulting in a selectivity of almost 1:1. The hardmask is thus necessary to increase the selectivity. Chromium is easy to deposit, pattern, and strip.

The Parylene probe outlines are then etched in Parylene insulating layer 306 by $O_2$ reactive ion etching as shown in View (E) of FIG. 3 to define the probe outline and expose the metal stacks 304 defining the interconnects and electrodes. After etching, as shown in View (F) of FIG. 3, the Chromium hardmask 308 is stripped and the flexible Parylene probes are released in View (G) of FIG. 3. The polymer layer can be peeled off of the wafer surface, leaving freestanding flexible probes. The released probes are then packaged with a custom designed printed circuit board (PCB) for electrical recording. Electrical connection between the PCB and the probe is established using Aluminum wedge wirebonding.

The final step is the integration of the flexible polymer probes with the stainless steel shuttles, which provides the mechanical support and rigidity for implantation. A stainless steel tube, preferably with an outside diameter of 500 microns and an inside diameter of 300 microns and between 4 cm and 12 cm in length is bisected along the axial direction to expose a semicircular inner channel. Preferably, the stainless steel tube will be bisected into equal portions to maximize the area available for mating with the Parylene probe. The channel is coated with heated (70° C.) PEG. Then the 260 microns wide flexible Parylene probe fabricated in accordance with the steps shown in FIG. 3 is aligned and placed inside the slot of the channel. A thin coating of PEG is used to encapsulate the probe and to ensure proper attachment to stainless steel shuttle.

The electrical performance of the probes has been characterized by electrochemical Impedance spectroscopy (EIS) measurements in IX PBS (Phosphate Buffered Saline) solution using 3 electrodes in the potentiostatic configuration. Electrochemical impedances of different channels of a typical probe were measured over a span of frequency ranging from 1 Hz-10 kHz by applying a 50 mV (rms) sinusoidal signal at open circuit potential (OCP).

Figure 4:
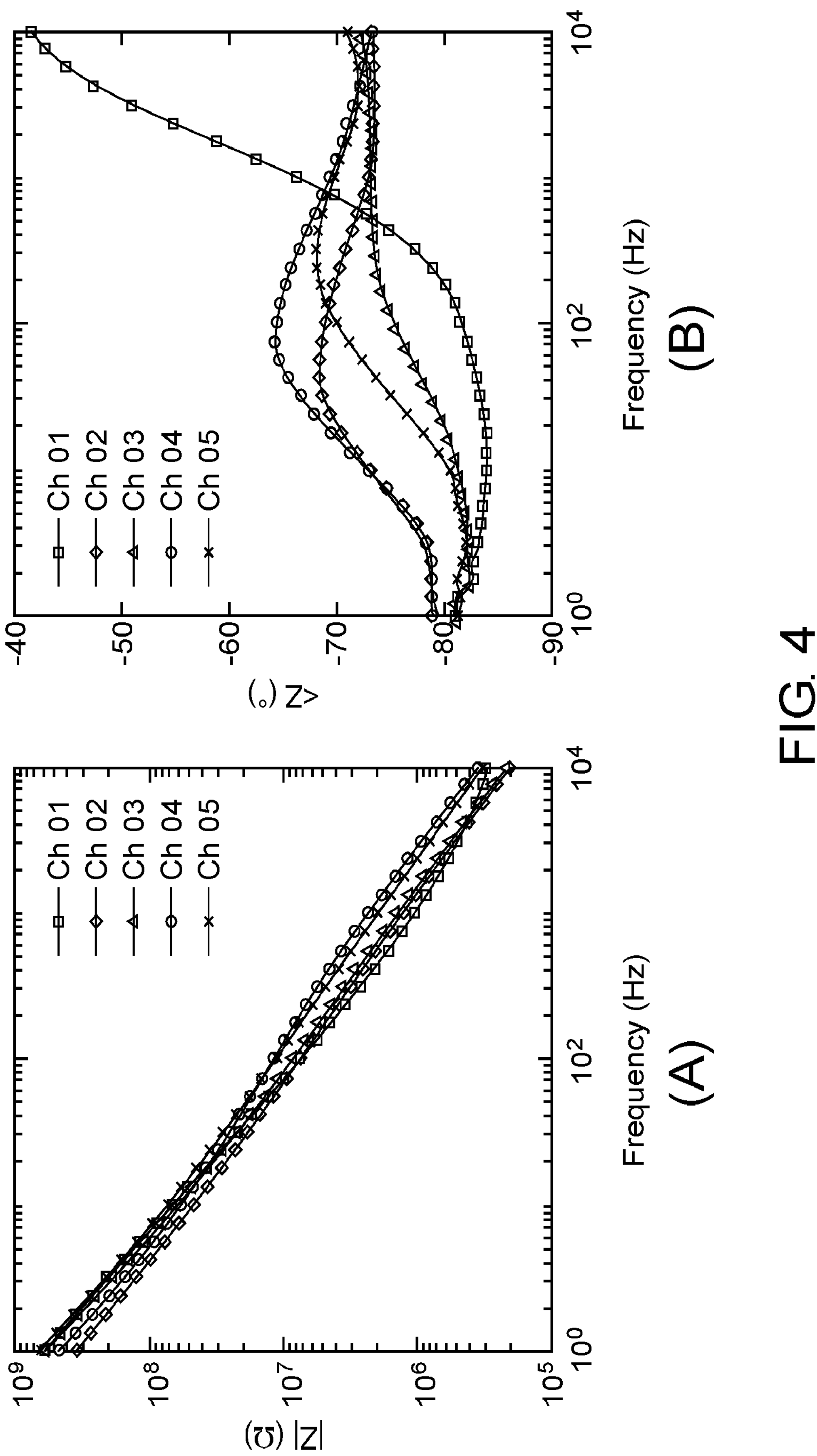
FIG. 4 shows graphs of the magnitude, in View (A), and the phase, in View (B), measurements of a subset of channels on a probe in accordance with this invention.

FIG. 4 shows graphs of the magnitude, in View (A), and the phase, in View (B), measurements of a subset of channels. A small variability of the impedance magnitude and phase can be observed between different channels. The magnitude of the average impedance of the functional channels were found to be 3 MΩ at 1 kHz. This value is consistent with previously reported results in literature for neural probes with similar electrode sizes. It should be noted that the small diameter of the electrodes was chosen to achieve higher spatial resolution and record single unit activities from neurons. However, since smaller electrodes have larger impedances, which can lead to low signal to noise ratios in the recorded neural signal. Post-fabrication surface modification techniques (i.e., PEDOT:PSS deposition) can be applied to achieve higher fidelity recording by reducing electrode impedances without changing its size.

While post-fabrication interfacing of high density probes on stainless steel shuttles provides the flexibility to realize 3D electrodes that can record from wider angles, the post-fabrication integration with stainless steel shuttles limits the throughput and scalability of manufacturing. To mitigate this issue, a second embodiment of a high-throughput method of monolithic processing in which the probes are fabricated directly on a stainless steel substrate is explained with reference to FIG. 5. This method provides a polymer probe stack directly on a stainless steel substrate. This embodiment, the stainless steel shuttle remains in the brain.

The surface roughness of commercially-available, unpolished stainless steel wafers prevents high-resolution microfabrication. The surface roughness makes it harder to define fine features required for fabricating high-density neural probes. Therefore, in one aspect of the invention, before commercially-available stainless steel wafers can be used in the fabrication of the neural probes, it must be planarized. Several different methods may be used for this purpose to enable high-resolution lithography and microfabrication.

In one aspect of the invention, different insulating materials can be spincoated to the surface of the stainless steel to planarize the stainless steel surface. Spincoating leads to a conformal film profile which covers and levels the topographic gaps on the substrate. Any of the following materials to achieve intended smoothing of stainless steel surface may be used: PDMS (Polydimethylsiloxane) is a porous material and has low surface energy, making it incompatible with high-resolution lithography. To fill the surface pinholes and functionalize the surface for lithography, an additional thin layer of Parylene C via may be deposited via chemical vapor deposition; Polyimide; spin-on-glass and epoxy. These materials can be spin-coated in liquid phase and then cured at higher temperature to solidify. In addition to providing a leveled surface for improved lithography resolution, these materials can also serve as the insulation layer of the neural probe architecture.

In a second aspect of the invention, planarization of stainless steel surface can be achieved by depositing a conformal layer of insulating materials such as Parylene C, Silicon Carbide, Silicon Oxide, Silicon Nitride, etc. These materials can be deposited via chemical vapor deposition or sputtering under different conditions. The conformal deposition process smoothens the sharp edges in the stainless steel topography, and the effect is increased by thicker layers of insulation. In alternate embodiments, two separate layers could be used, one for planarization and another on top for electrical insulation. In practice, because all of the planarization layers are insulating, one layer may serve both purposes.

In yet another aspect, chemical mechanical polishing (CMP) can also be utilized to reduce the surface roughness of stainless steel. This can be achieved through chemical oxidation and mechanical abrasion using a chemical slurry.

In yet another aspect, electropolishing can be used to planarize the stainless steel surface. In this process, the stainless steel sample is used as an anode and submerged in an electrolytic solution at a controlled temperature in the presence of another cathodic conductor. Then, direct current is flowed through the circuit which causes the removal of surface imperfections and contaminants from the stainless steel surface. A similar process can be utilized in caustic solution to "anodize" stainless steel. In this process, the natural oxide layer on stainless steel is thickened, which results in a reduction of surface roughness. Moreover, corrosion resistance is improved due to the increased passivation.

Figure 5:
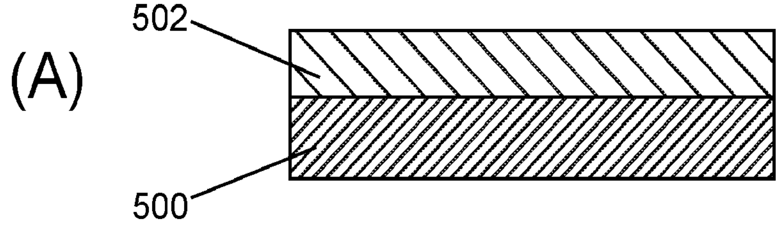
FIG. 5 shows a step-by-step application progress for probes in accordance with a second embodiment of the invention in which the probes are fabricated directly on a stainless steel substrate.
Figure 5:
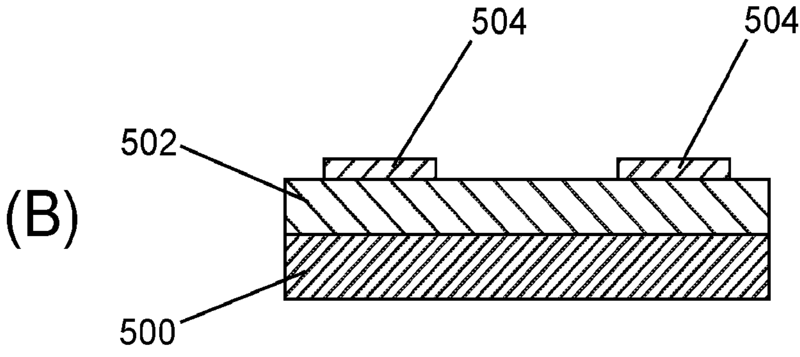
Figure 5:
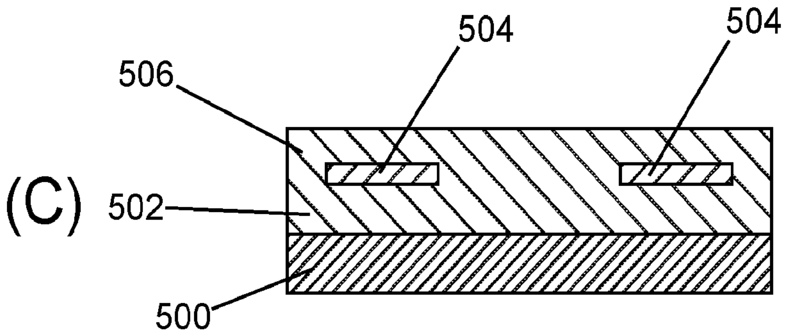
Figure 5:
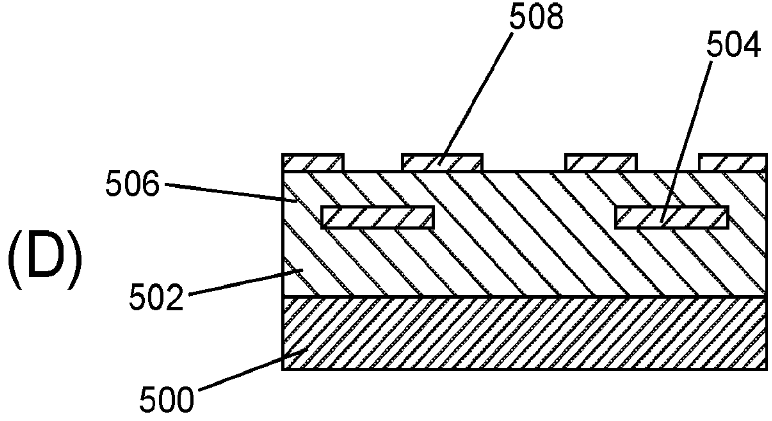
Figure 5:
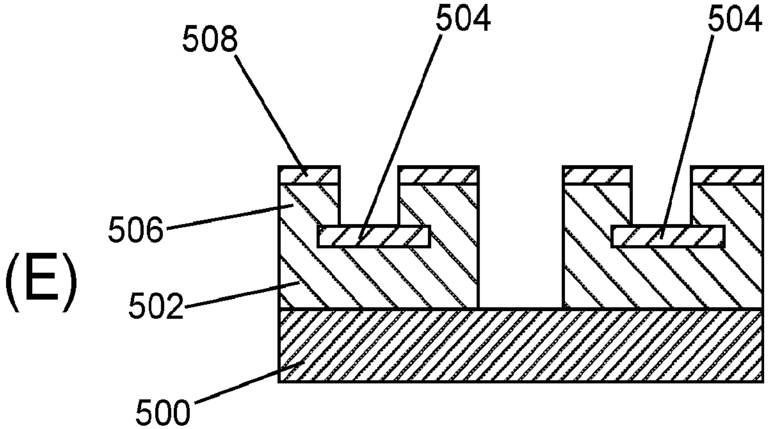
Figure 5:
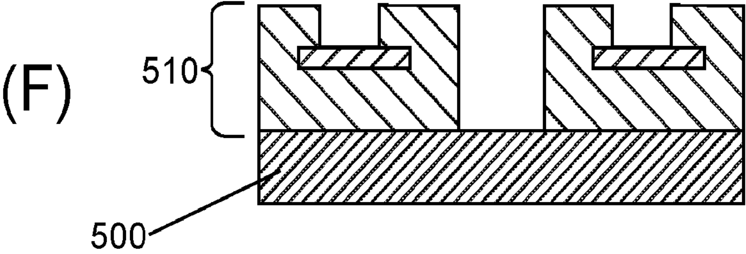
Figure 5:
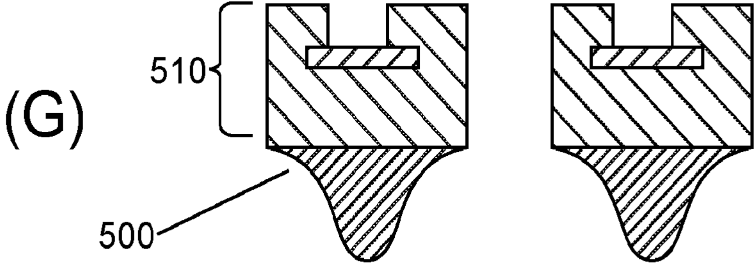

The fabrication of monolithic probes on stainless steel follows a similar process as shown in FIG. 3 for realizing the polymer-based probe, except for the substrate which is a 125 μm thick stainless steel wafer that will be singulated at the end of the process. First, substrate 500 is functionalized with a thin layer of Silane A 174 adhesion promoter to increase the adhesion with the thin layer of Parylene C insulation 502, as shown in View (A) of FIG. 5. In other embodiments, where alternates to Parylene C as used, the step may be unnecessary. The metal traces and recording electrodes 504 are then lithographically patterned on Parylene layer 502, as shown in View (B) of FIG. 5, using the same Pt/Au/Pt combination of metals discussed above. Thereafter, an insulating layer of Parylene C 506 is deposited, as shown in View (C) of FIG. 5, which will be etched to define the outline of the probes. View (D) of FIG. 5, shows the deposition of the hardmask of Chromium 508 on the insulating layer of Parylene 506 for subsequent Parylene etching. The Chromium hardmask 508 is photolithographically patterned to define the probe outline as well as electrode recording sites and bondpad openings.

The Parylene probe outlines are then etched in Parylene insulting layer 506 by $O_2$ reactive ion etching as shown in View (E) of FIG. 5 to define the probe outline and expose the metal stacks 304 defining the interconnects and electrodes. After etching, as shown in View (F) of FIG. 5, the Chromium hardmask 508 is stripped.

The final step of the process is to singulate each hybrid Parylene-Stainless Steel probe 510 from the stainless steel substrate 500 using a novel stainless steel etching process. This may be accomplished using a precision laser to cut and shape the stainless steel wafer. Alternatively, electrochemical etching may be used for this purpose.

The optimized etching process yields a smooth and curved surface shuttle, shown in View (G) of FIG. 5, that facilitates safe implantation of the probe into the tissue without cutting the vasculature and the tissue.

Figure 6:
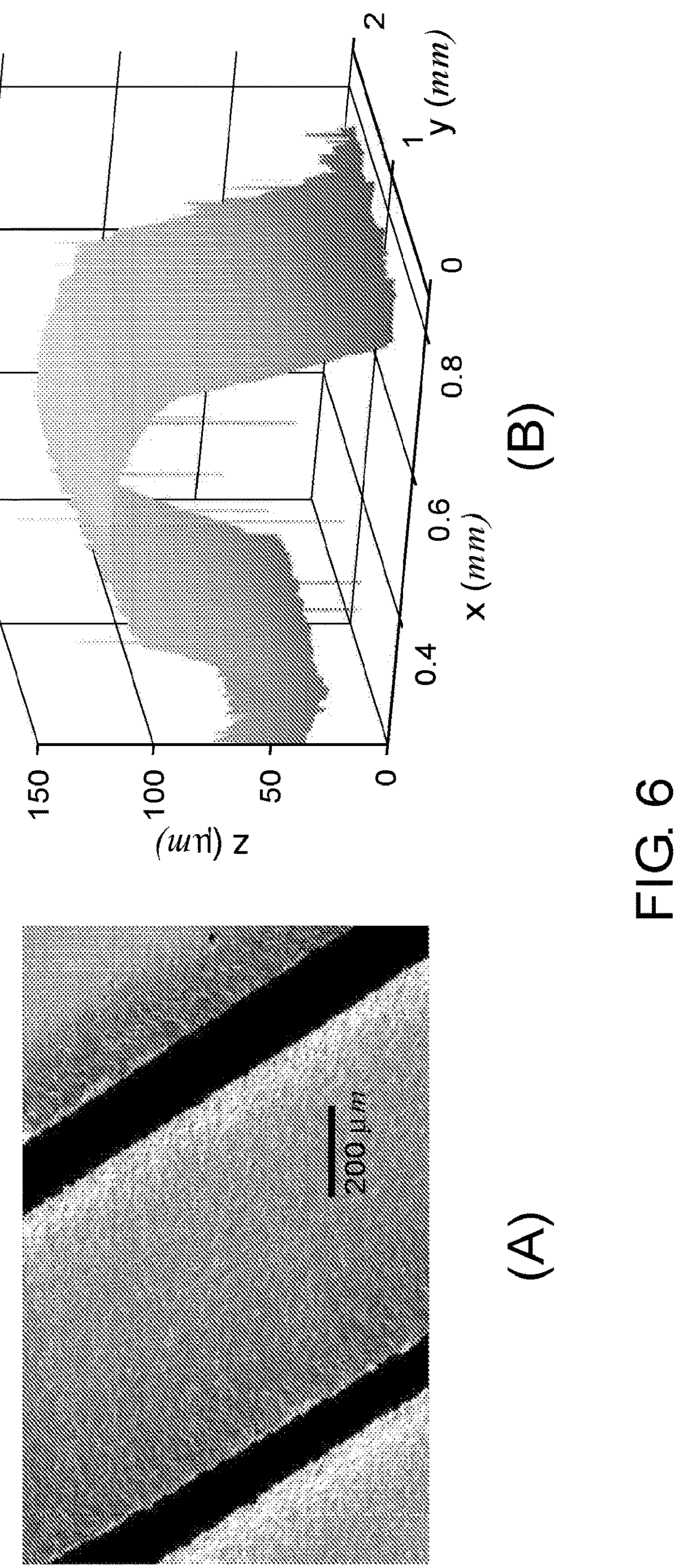
FIG. 6 shows, in View (A), a scanning electron micrograph (SEM) and, in View (B), a 3D surface profile of an etched probe shank.

FIG. 6 shows, in View (A), a scanning electron micrograph (SEM) and, in View (B), a 3D surface profile of an etched probe shank, where the two through trenches define the outline of the probe shank. To reduce the tethering force on the probe and to minimize damage to brain tissue due to micromotion, part of Stainless steel reinforcement underneath the Parylene cable near probe backend is released. This way, a flexible Parylene cable connects the stainless steel shank to the rigid backend as shown in FIG. 1. The stainless steel probe shank helps with the implantation of the probe by providing the necessary stiffness and the flexible Parylene tether cable connects to the neural recording electronic circuitry ensuring minimal strain on the probe.

Figure 7:
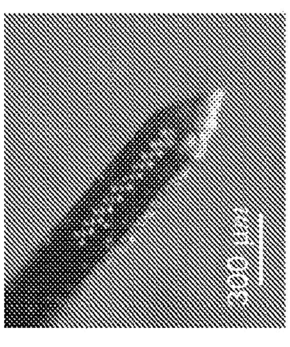
FIG. 7 shows several views of different configurations for possible placement of the channels on the service of the probe.
Figure 7:
Figure 7:
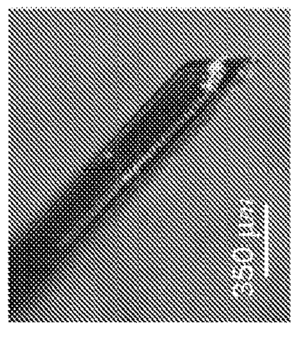
Figure 7:
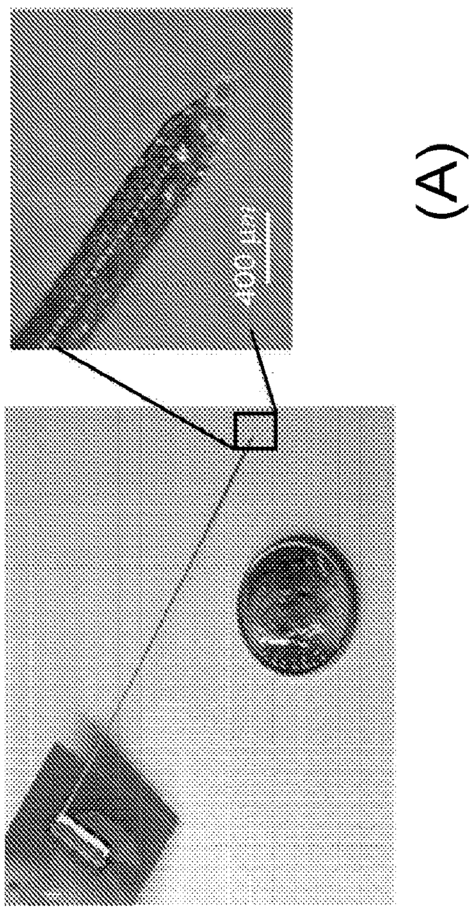
Figure 7:

Channels may be etched on the Parylene layer in various different configurations. FIG. 7 shows several different configurations that may commonly be used. In View (A), a linear configuration longitudinally disposed on the service of the probe is shown. View (B) show a linear configuration of channels disposed on the edge of the probe, and View (C) shows a honeycomb configuration longitudinally disposed on the surface of the probe.

As would be recognized by one of skill in the art, the above description is exemplary in nature only. Different combinations of materials and dimensions of the probes and components of the probes, as well as the configuration of the channels on the service of the probe may be used and will still be within the scope of the invention which is defined by the claims which follow.

We claim:

1. A neural probe comprising:

a probe device comprising:

a substrate composed of Parylene C;

one or more multi-layer metal stacks comprising a first layer of platinum, a layer of gold and a second layer of platinum, deposited onto the substrate, the metal stacks each being patterned to define an electrode, interconnect and an electrical trace connecting the electrode and the interconnect; and an insulating layer composed of Parylene C and deposited on the substrate and the metal stacks, the insulating layer patterned to expose the electrodes and interconnects; and a shuttle comprising:

a stainless steel tube bisected along an axial direction to expose a semicircular inner channel; and a bioresorbable polymer coating the inner channel;

wherein the probe device is disposed in the inner channel of the shuttle and held therein by the bioresorbable polymer;

the neural probe further comprising:

a coating of the bioresorbable polymer disposed on the probe device and encapsulating the probe device in the inner channel of the shuttle.

2. The neural probe of claim 1 further comprising a printed circuit board to which the one or more interconnects are connected.

3. The neural probe of claim 1 wherein the shuttle has an outer diameter of approximately 500 microns and an inner diameter of approximately 300 microns.

4. The neural probe of claim 1 wherein the shuttle is between 4 cm and 12 cm in length.

* * * * *